United States Patent [19]

Squyres

[11] Patent Number: 5,440,127

[45] Date of Patent: Aug. 8, 1995

[54] METHOD AND APPARATUS FOR ILLUMINATING TARGET SPECIMENS IN INSPECTION SYSTEMS

[75] Inventor: Henry P. Squyres, Medford, Oreg.

[73] Assignee: Simco/Ramic Corporation, Medford, Oreg.

[21] Appl. No.: 63,401

[22] Filed: May 17, 1993

[51] Int. Cl.⁶ .......................................... G01N 21/35
[52] U.S. Cl. ................. 250/341.8; 250/910; 356/407
[58] Field of Search ............. 356/402, 407, 425; 209/576, 577, 578, 580, 581, 582; 250/341.8, 910

[56] References Cited

U.S. PATENT DOCUMENTS

| | | | |
|---|---|---|---|
| 3,675,769 | 7/1972 | Story | 209/577 |
| 3,773,172 | 11/1973 | McClure et al. | 209/580 |
| 4,057,352 | 11/1977 | Babb | 356/407 |
| 4,186,836 | 2/1980 | Wassmer et al. | 209/565 |
| 4,262,806 | 4/1981 | Drabs | 209/577 |
| 4,279,346 | 7/1981 | McClure et al. | 209/582 |
| 4,738,175 | 4/1988 | Little et al. | 83/71 |
| 5,085,325 | 2/1992 | Jones et al. | 209/580 |
| 5,134,291 | 7/1992 | Ruhl, Jr. et al. | 250/341 |
| 5,141,110 | 8/1992 | Trischan et al. | 209/524 |

OTHER PUBLICATIONS

Yoshinori Anzai, Takeo Saikatsu, Hiroyoshi Yamazaki, Keiji Watanabe, "Rare Gas Discharge Lamps Suitable for Industrial Use," Lighting Design & Applicaiton, Feb. 1987, pp. 33-38.

*Primary Examiner*—F. L. Evans
*Attorney, Agent, or Firm*—Stoel Rives Boley Jones & Grey

[57] ABSTRACT

An illumination system (12) for an optical inspection and sorting apparatus (10) includes a rare gas discharge lamp (36) for emitting select wavelengths of radiation. Rare gas discharge lamp (36) includes a light transmissive outer envelope (58) and contains one or more rare gases, and in particular neon, argon, or xenon. A hemi-elliptical reflector (48) having reflecting surface (38) directs the select wavelengths of radiation toward target specimens (16) in optical scanning area (24) in illumination area (20).

17 Claims, 1 Drawing Sheet

METHOD AND APPARATUS FOR ILLUMINATING TARGET SPECIMENS IN INSPECTION SYSTEMS

TECHNICAL FIELD

The present invention relates to methods and apparatus for use in connection with optical inspection and sorting systems and, in particular, to a method and an apparatus for illuminating specimens during inspection and sorting operations.

BACKGROUND OF THE INVENTION

Automated optical inspection and sorting systems have been used to inspect and sort various target specimens including fruits and vegetables, processed meats, baked goods, and other foodstuffs, to separate different types of recyclable material, and to sort foreign or defective items from supplies of wood chips. These systems typically employ video cameras with charge-coupled device line scan cameras to acquire images of target specimens moved on a conveyor belt across an optical scanning area. Illumination of the specimens is generally provided by broad-spectrum fluorescent lamps. Signal processing circuitry identifies variations in the shade of target specimen images and sorts target specimens accordingly.

Inspection and sorting systems utilizing color images are well suited to inspecting and sorting specimens when the unacceptable and acceptable items are characterized by subtle differences in color, shade, and hue. Progress in detecting subtle variations in color has improved the precision and quality of color inspection and sorting systems. Such progress has also reduced the waste among specimens processed by such color inspection and sorting systems. These recent improvements in color sorting precision have not always also resulted in increased sorting speed.

Another area of ongoing development in optical inspection and sorting system is directed toward increasing the processing efficiency, that is, the quantity of target specimens inspected and sorted per unit time. Advances in signal processing techniques provide some increases in the speed at which images of the specimens can be acquired and processed. However, increased image acquisition speeds result in diminished scanning time for each individual target specimen and, consequently, a reduction in the amount of light received by photoreceptors from the target specimens. Illumination of target specimens thus becomes important.

Light intensity at a target specimen varies as the inverse square of the distance from the light source. Inspection and sorting systems having video cameras and light sources positioned at a distance from the target specimens, for example, to view a sufficiently large surface area, generally suffer a substantial decrease in the intensity of light received from the inspection area and target specimens. Increases in image acquisition speeds and video camera and light source position therefore must be carefully coordinated to improve the performance of inspection and sorting systems.

Optical defect inspection systems typically employ conventional tubular fluorescent lamps to illuminate the specimen inspection field. Such conventional fluorescent lamps include, for example, Sylvania cool-white VHO fluorescent lamp model F 72 T 12 (212 watts) available from GTE Electrical Products, One Stamford Forum, Stamford, Conn. 06904 and similar cool-white VHO fluorescent lamps available from North American Phillips, Phillips Lighting Products, 200 Franklin Sq. Dr., Sommerset, N.J. 08875. Conventional tubular fluorescent lamps emit a broad spectrum of radiation and typically comprise a large-diameter elongated tube with a layer of phosphorous material coating an inner surface. Conventional fluorescent light sources are inefficient in the context of optical defect and inspection systems because they waste unacceptably large quantities of their radiated light energy. The unacceptable losses occur for several reasons.

Much of the radiation emitted from conventional fluorescent lamp sources in optical inspection systems is absorbed by the conveyor belt and portions of the target specimens that are not visible to the image acquisition sensors of the video camera. Absorbed radiation can shorten the useful life of the conveyor belt and the shelf or storage life of the target specimen. Furthermore, much of the broad-spectrum radiation emitted by conventional fluorescent sources that is reflected by the surface of the target specimens does not contribute to the sorting decision. That is, much of the reflected light contributes little information useful for inspection and sorting decisions. At the same time, conventional broad-spectrum sources often provide insufficient radiation of those wavelengths that do contribute to distinguishing the features upon which sorting decisions are based. As a result of limitations in illumination of target specimens, automated inspection and sorting equipment employing conventional fluorescent lamps is often unable to keep pace with the increased image acquisition and processing capabilities of current and emerging technologies.

A phosphor or other coating on the inner surface of the tubular glass envelope of a conventional fluorescent lamp is adapted to emit visible light upon absorption of ultraviolet radiation that is produced when the lamp electrodes, which typically contain mercury or other emissive material, are ionized by application of an electrical current. The phosphor coating on the inner surface of the lamp envelope fluoresces and reemits a substantial portion of the ultraviolet radiation as visible light. The spectral characteristics of the visible light are determined principally by the composition of the fluorescent powders used for the phosphor coating. In inspection systems employing conventional fluorescent lamps as the only source of illumination, relatively few of the wavelengths of visible light emitted by the fluorescent lamp are used for the inspection and sorting decisions. In some such systems, bandfilter or other color-selective filters are used to cull the useful wavelengths from the many wavelengths emitted.

Conventional fluorescent lamps also have the disadvantage that luminous output degenerates over time and is temperature dependent. Moreover, conventional fluorescent lamps have a slow response time at start-up. The resulting inadequate and inconsistent lighting can significantly reduce the accuracy of inspection and sorting decisions.

Laser-based illumination systems are capable of directing high-intensity light at target specimens but are typically expensive and ineffective for inspection and sorting that requires multiple wavelengths of light. The range and variety of spectral output from currently available laser-based illumination systems is limited. The surface area that can be effectively illuminated by laser-based illumination systems also is limited.

SUMMARY OF THE INVENTION

An object of the present invention is, therefore, to provide an optical inspection and sorting system that can take advantage of improved signal processing technology and provide increased throughput of target specimens.

Another object is to provide a method and apparatus for efficiently illuminating a target specimen in an optical inspection and sorting system.

A further object of this invention is to provide such a method and apparatus for emitting and directing radiation of select wavelengths toward a target specimen to enhance the differentiation of target specimens and to increase sorting speed and accuracy.

Still another object of this invention is to improve overall process efficiency by providing an illumination source that emits primarily radiation having wavelengths that provide useful information to the inspection and sorting decision.

An additional object of the present invention is to direct the illumination source to maximize the illumination of target specimens.

Another object of the present invention is to increase the versatility of inspection and sorting systems by providing specific illumination sources emitting select wavelengths of radiation according to the particular inspection and sorting task.

According to the present invention, an illumination system for an optical inspection and sorting apparatus includes a high-intensity rare gas glow discharge lamp for emitting radiation of select wavelengths. In one preferred embodiment, the rare gas discharge lamp of the current invention contains one or more of the rare or noble gases such as helium, neon, argon, or xenon. The rare gas discharge lamps of the present invention preferably have a smaller diameter than conventional fluorescent tubes and contain no significant absorbent or fluorescent materials coating the inner surface of the transmissive envelope confining the rare gas.

Illumination sources of the present invention primarily emit radiation having wavelengths that provide useful information for the inspection and sorting decisions. The illumination system of the present invention may also include a hemi-elliptical light-reflecting surface for reflecting radiation toward the target specimens in an optical scanning area. Light that would otherwise be dissipated is thereby directed toward target specimens visible to the image acquisition sensors of the camera.

Additional objects and advantages of the present invention will be apparent from the following detailed description of a preferred embodiment thereof, which proceeds with reference to the accompanying drawings.

DETAILED DESCRIPTION OF A PREFERRED EMBODIMENT

Figure 1:
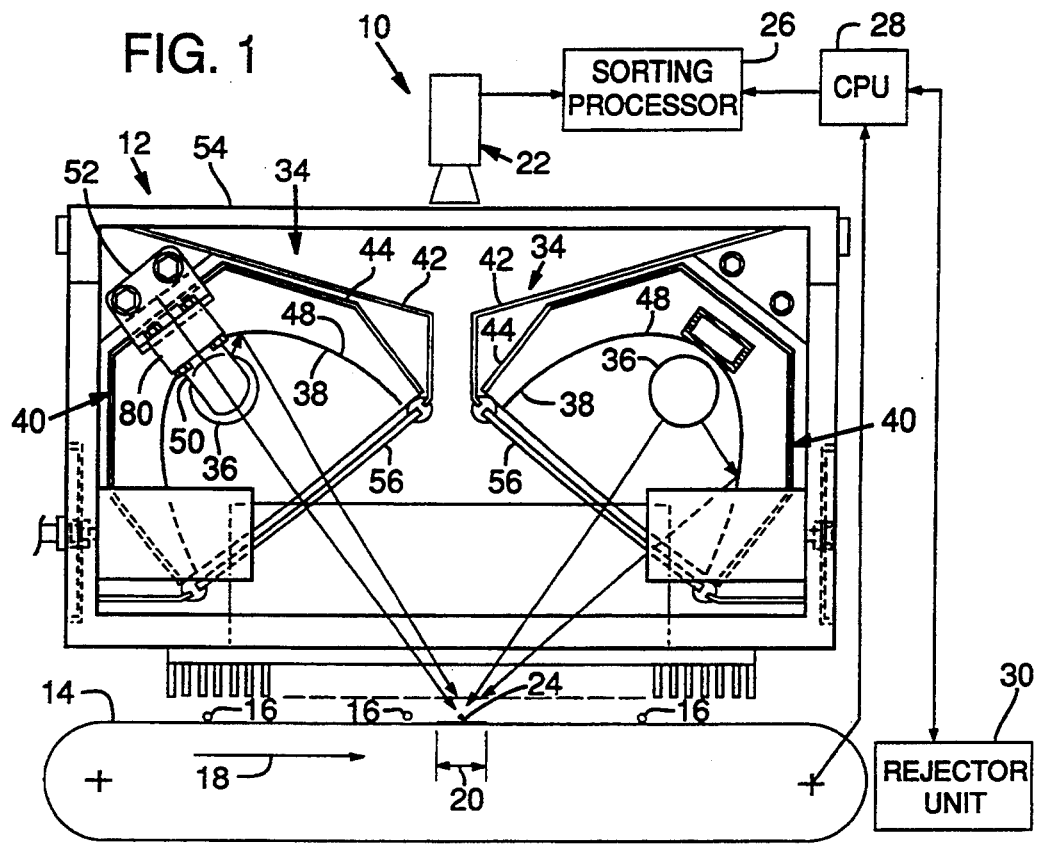
FIG. 1 is a schematic diagram showing an end elevation view of an optical inspection system that includes an illumination system of the present invention.
Figure 2:
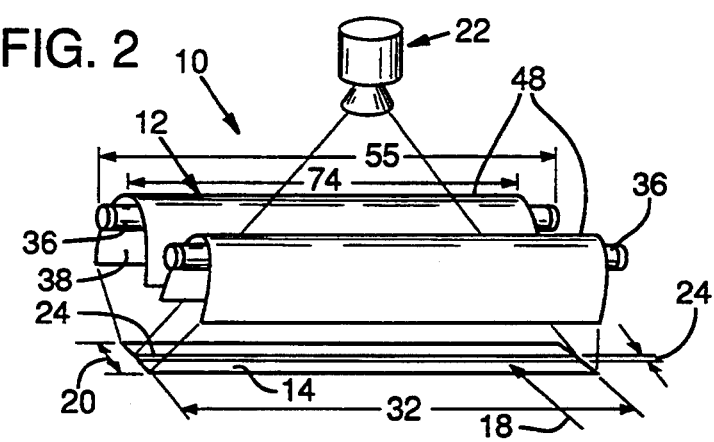
FIG. 2 is a front elevation view of the illumination system shown in FIG. 1, with parts removed for clarity.

FIGS. 1 and 2 show an optical inspection system 10 incorporating a preferred embodiment of an illumination system 12 of the present invention. Inspection system 10 may be of the specimen inspection and sorting type described in U.S. Pat. No. 4,738,175 to Little et al. for a "Defect Detection System" and U.S. Pat. No. 5,085,325 to Jones et al. for a "Color Sorting System and Method," both assigned to the assignee of the present application and herein incorporated by reference.

Inspection system 10 employs an endless conveyor belt 14 to move target specimens 16 in a direction 18 across an illumination area 20. Inspection system 10 sorts and separates target specimens 16, such as blueberries, that are moved by conveyor belt 14 as quickly as 500 feet per minute across illumination area 20. A panchromatic line scan video camera 22 scans target specimens as they pass through a scanning area 24 within illumination area 20.

Images of target specimens 16 are acquired by video camera 22. Sorting processor 26 processes image data generated by video camera 22 and arranged in image frames containing any desired number of scan lines. A central processor unit 28 linked with sorting processor 26, conveyor belt 14, and a rejector unit 30 synchronizes the timing of the position of target specimens 16 with the operation of rejector unit 30. Rejector unit 30 sorts target specimens 16 when sorting processor 26 determines that those target specimens include certain selected physical features such as spectral reflectance or absorption, size, or shape.

The selected physical features form the basis for sorting decisions and are characterized by the optical response of the target specimens including recognizable patterns of reflection and absorption of radiation. The optical response of a target specimen to radiation of a particular wavelength, including any recognizable patterns of reflection and absorption of the particular wavelength of radiation, can signify defects such as, for example, the presence of a soft center in undercooked potato chips or the presence of grape stems among raisins. Such patterns can also be used to detect the presence of leaves and twigs among blueberries and in a variety of other sorting applications.

Illumination system 12 of the present invention includes multiple light source assemblies 34 positioned to project radiant energy along the width of conveyor belt 14 at scanning area 24 in illumination area 20. Each light source assembly 34 includes a nonfluorescing rare gas discharge lamp 36 for emitting high-intensity radiation of select wavelengths that reflects off an inner light-reflecting surface 38 of a shroud-like reflector structure 40 and is directed toward illumination area 20. Rare gas discharge lamp 36 is cooled by forced air.

Rare gas discharge lamp 36 contains a rare or noble gas or a mixture of rare gases. Each rare gas and each mixture of rare gases emits select wavelengths of high-intensity radiation when ionized at the breakdown voltage. Rare gas discharge lamp 36 emits radiation with an intensity approximately two to three or more times than that of conventional fluorescent sources. In one embodiment, rare gas discharge lamp 36 containing primarily neon emits approximately 17 milliwatts per square cm (centimeter) of radiation having wavelengths of approximately 400 nm (nanometers) to 1100 nm, measured at the focal plane of target specimens 16. The intensity of radiation reflecting from target specimens 16 depends on the distance between rare gas discharge lamp 36 and target specimens 16. A particular rare gas or mixture of rare gases and the distance between rare gas discharge lamp 36 and target specimens 16 are chosen according to the specific intended application of inspection and sorting system 10. More specifically, when rare gas discharge lamp 36 contains neon or argon, lamp 36 emits high-intensity radiation in the red or near infrared regions of the electromagnetic spectrum. The radiation emitted from rare gas discharge lamp 36 containing, for example, neon plus 0.1 percent argon at a pressure of 665 Pa (Newtons per square meter ($N/m^2$)) (approximately 5 Torr), concentrates predominately in the red range of the electromagnetic spectrum from 580 nm to 780 nm with a major spike at about 640 nm. The radiation emitted from rare gas discharge lamp 36 containing, for example, 50 percent neon and 50 percent argon at a pressure of 665 Pa ($N/m^2$) (approximately 5 Torr), concentrates predominately in the near infrared range from approximately 700 nm to approximately 1000 nm with a major spike at about 810 nm and a minor spike at about 760 nm.

One embodiment of rare gas discharge lamp 36 is particularly well suited for inspection and sorting decisions based upon differentiating materials such as blueberries or other small dark fruit from chlorophyll-containing materials such as twigs and leaves. Molecules of chlorophyll A and chlorophyll B absorb some of the wavelengths of light in the red region (600 nm to 700 nm) and in the blue region (400 nm to 500 nm) of the electromagnetic spectrum, but both molecules reflect almost all wavelengths of light in the yellow and green regions (500 nm to 600 nm).

Another embodiment of rare gas discharge lamp 36 containing neon or a rare gas mixture including neon is particularly well suited to differentiating fully cooked potato chips from soft-centered or undercooked potato chips. Soft-centered potato chips reflect wavelengths of radiation in the red region of the electromagnetic spectrum; fully cooked potato chips substantially absorb wavelengths of radiation in the red region. In particular, soft-centered potato chips absorb radiation between approximately 650 nm and 750 nm; fully cooked potato chips reflect radiation between approximately 650 nm and 750 nm.

Other embodiments of rare gas discharge lamp 36 containing primarily argon or primarily xenon are well suited to differentiating raisins from grape stems. Stems reflect wavelengths of radiation in the region between approximately 800 nm to approximately 1100 nm; relative to grape stems, raisins absorb wavelengths of radiation in the region of from approximately 800 nm to approximately 1100 nm. Rare gas discharge lamp 36 containing primarily xenon or primarily argon emits high-intensity radiation of wavelengths from approximately 800 nm to 1100 nm.

Reflector structure 40, which fits within and is supported by an outer covering 42 of light source assembly 34, includes a housing 44 and a preferably hemi-elliptical reflector 48 secured within housing 44. Each rare gas discharge lamp 36 may be held in place by, for example, a pair of tube sockets 50 that are supported by a light source support member 52 connected to frame 54. The length 55 of rare gas discharge lamp 36 is generally a function of and typically greater than length 32 of scanning area 24.

Rare gas discharge lamp 36 is positioned within rectangular frame 54 so that lamp 36 lies in a direction generally perpendicular to conveyor belt travel direction 18 to illuminate target specimens 16 as they are scanned by video camera 22. Radiation from rare gas discharge lamp 36 propagates directly toward illumination area 20. Radiation also propagates toward and reflects from light-reflecting surface 38 of hemi-elliptical reflector 48 toward illumination area 20. Hemi-elliptical reflectors 48 have lengths 74 that are about equal to length 32 of scanning area 24 and about equal to or shorter than length 55 of rare gas discharge lamp 36. Because reflectors 48 are of hemi-elliptical shape, reflectors 48 produce a line focus of light that strikes illumination area 20 and scanning area 24 on conveyor belt 14.

Rare gas discharge lamp 36 also typically has a smaller diameter than conventional broad-spectrum fluorescent tubes. When used with hemi-elliptical reflectors, smaller diameter lamps come closer to approximating a line source of illumination than larger diameter lamps. Line sources are more efficient than diffuse sources of illumination.

Preferably, an optically transmissive protective covering 56 encloses reflector structure 40 to protect target specimens 16 from debris falling from a broken rare gas discharge lamp 36. Also, hemi-elliptical reflector 48 supports a preformed aluminum substrate that carries on its inner surface 38 a light-reflective coating such as, for example, the "BV2 coating" having 89 to 93 percent reflectivity, which is produced by Optical Coating Labs, Inc. of Santa Rosa, Calif.

Figure 3:
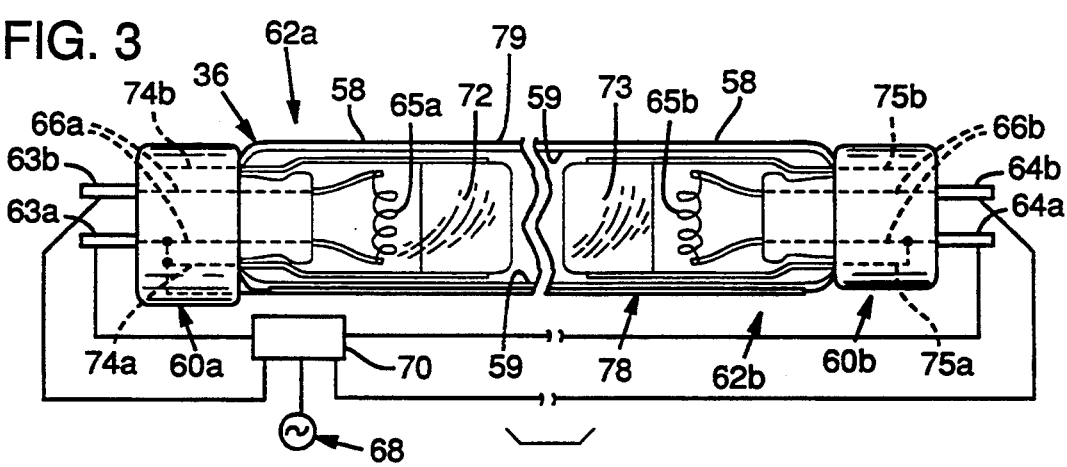
FIG. 3 is a simplified side view of a rare gas discharge lamp of the present invention with associated electrical components shown schematically.

Referring to FIG. 3, rare gas discharge lamp 36 comprises a light-transmitting, gas-impervious tubular outer envelope 58, which may be of generally round, oblong, ovoid, figure-eight, or other cross-section, shape, or configuration and is formed preferably of hard or soft optically transmissive glass or quartz. In one preferred embodiment, outer envelope 58 is approximately 175 cm (centimeters) in length and has an outer diameter of approximately 20 mm (millimeters) with walls 1.6 mm thick. Envelope 58 is filled with one or more of the rare or noble gases such as neon, argon, xenon, krypton, or helium following procedures known in the art such as are described in "Neon Techniques and Handling" by Samuel C. Miller (1990) available from Sign-of-the-Times Publishing Co., 407 Gilbert Avenue, Cincinnati, Ohio 45202. Unlike conventional fluorescent lamps, rare gas discharge lamp 36 is preferably formed without a phosphor layer or layer of other absorbent or fluorescent material on inner surface 59 of light-transmitting tubular outer envelope 58.

Secured to opposed ends of outer envelope 58 are bases 60a and 60b. Bases 60a and 60b extend between electrode structures 62a and 62b respectively and pairs of pins 63 and 64, respectively. Lamp socket 50 (FIG. 1) provides electrical energy to rare gas discharge lamp 36 through respective pairs of pins 63 and 64. In one preferred embodiment, electrode structures 62a and 62b are model HI 800 MA electrodes available from EGL in Newark, N.J. Electrode filaments 65a and 65b are connected to respective pairs of pins 63 and 64 by respective pairs of filament electrode leads 66a and 66b.

Rare gas discharge lamp 36 is excited by means of the application of a voltage between electrode filaments 65a and 65b. Current flows between filaments 65a and 65b after a certain acceptable potential, or breakdown voltage, is applied between filaments 65a and 65b by light source driver 68 through ballast 70. The rare or noble discharge gas creates an electrically conductive path between filaments 65a and 65b when the gas ionizes at the breakdown voltage. Ballast 70 transforms the external source of alternating current to the voltage level necessary to operate rare gas discharge lamp 36. Filaments 65a and 65b are each connected by way of respective pair of filaments leads 66a and 66b to ballast 70 and light source driver 68. Ballast 70 converts 115-volt commercial voltage into a high starting voltage, current-limited lower operating voltages, and heater voltages. Example voltages are a starting voltage of approximately 2500 VAC at approximately 50 KHz, an operating voltage of from approximately 400 to 1000 volts with a current of approximately 50 milliamps to 1000 milliamps, and a heater voltage of approximately 6 volts.

Rare gas discharge lamps such as the neon tubes used in neon signs are typically driven by very high output (VHO) ballasts or other high-frequency light source drivers. VHO ballasts often allow several cycles of illumination to be integrated by a line scan camera during acquisition of a line image so that the effective illumination will be uniform. However, VHO ballasts are undesirable because they suffer from a too low starting voltage. In a preferred embodiment, ballast 70 is model 16144-2 available from Mercron of Richardson, Tex., which will power two standard fluorescent lamps commonly driven by a 60-Hertz power source. Such drivers have a photocell feedback circuit that monitors the average light output of the fluorescent bulb to automatically boost or reduce the drive current to maintain a constant light output.

Bombardment electrode 72 includes pair of bombardment electrode leads 74a and 74b; bombardment electrode 73 includes pair of bombardment electrode leads 75a and 75b. Bombardment electrode leads 74a and 75a are electrically connected through light source driver 68 and ballast 70. Bombardment electrodes 72 and 73 remove impurities from rare gas discharge lamp 36 prior to real-time operation by high voltage discharge. During real-time operation bombardment electrodes 72 and 73 contribute to the ionization of the discharge gas. In an alternate embodiment, impurities may be removed from light-transmitting tubular outer envelope 58 by baking at elevated temperatures, for example 500° C., under a vacuum prior to filling with rare or noble gases.

An electrically conductive film ground plane 78 adheres to the outer surface 79 of light-transmitting outer envelope 58 and extends substantially the full length of outer envelope 58. Ground plane 78 is electrically connected to bombardment electrode lead 74a. Ground plane 78 is preferably approximately 15 mm wide and constructed of aluminum foil or other suitable material. Ground plane 78 serves to facilitate ionization of the discharge gas and allows activation of rare gas discharge lamp 36 at a significantly lower voltage than would be possible otherwise.

Rare gas discharge lamp 36 plugs into tube socket 50 of lamp fixture 80 designed to support discharge lamp 36 and to supply electric current to electrode filaments 65a and 65b and to bombardment electrodes 72 and 73. Lamp fixture 80 may include ballast 70.

The output of light radiation from conventional fluorescent lamps, relative to the maximum output, is dependent upon temperature. The output of rare gas discharge lamp 36 is largely independent of temperature. Rare gas discharge lamp 36 is therefore more thermal-stable than conventional fluorescent lamps. Rare gas discharge lamp 36 also has a shorter start-up time than conventional fluorescent lamps. The output of light radiation from rare gas discharge lamp 36 does not significantly decrease over time as compared with conventional fluorescent lamps. In a preferred embodiment, rare gas discharge lamp 36 does not produce unwanted radiation in the visible mercury spectrum, which does not contribute useful information for the inspection and sorting decision.

The relative lighting efficiency of rare gas discharge lamp 36 is a function of the pressure and composition of the rare gas mixture contained within light-transmitting tubular outer envelope 58. Generally, there is greater efficiency at lower filling gas pressures. The relative lighting efficiency for rare gas discharge lamp 36 is dependent on the current. Because the lamp voltage can be changed with the gas composition, rare gas discharge lamp 36 can be engineered to satisfy varying needs for both wattage and dimensions.

It will be obvious to those having skill in the art that many changes may be made in the above-described details of a preferred embodiment of the present invention without departing from the underlying principles thereof. For example, illumination system 12 may also comprise multiple video cameras 22 or a single light source 36 and hemi-elliptical reflectors 48 and light source 36 at various distances and angles from conveyor belt 14. Illumination system 12 also can be combined with other types of illumination systems. The scope of the present invention, therefore, should be determined only by the following claims.

I claim:

1. A method of operating an automated optical inspection system to separate selected items from a mixture including blueberries and the selected items, comprising:

illuminating the mixture with illumination characterized by a spectral power distribution including a high intensity of power at wavelengths in the near infrared;

detecting reflections of wavelengths of the illumination in the near infrared from the mixture;

identifying the selected items in the mixture based on the detected reflections; and separating the selected items from the mixture with use of the identification.

2. The method of claim 1, wherein the selected items include vegetable matter containing chlorophyll.

3. The method of claim 1, wherein the blueberries comprise ripe blueberries.

4. The method of claim 1, wherein the selected items reflect the power of the illumination in a spectral range of from about 500 nm to about 600 nm.

5. The method of claim 1, wherein the selected items absorb the power of the illumination in a spectral range of from about 400 nm to about 700 nm.

6. The method of claim 1, further comprising producing the illumination with a hot-cathode rare gas discharge lamp.

7. A method of operating an automated optical inspection system to separate selected items from a mixture including blueberries and the selected items, comprising:

illuminating the mixture with high-intensity illumination from a hot-cathode rare gas discharge lamp, said illumination being in the near infrared and characterized by a spectral power distribution;

resolving with the illumination selected items in the mixture;

identifying the resolved selected items with the illumination; and separating the resolved selected items from the mixture with use of the identification.

8. The method of claim 7, wherein substantially all of the power in the illumination is at wavelengths within a spectral range of from about 400 to about 1100 nm.

9. The method of claim 7, wherein substantially all of the power in the illumination is at wavelengths within a spectral range of from about 700 to about 1000 nm.

10. The method of claim 7, wherein a significant fraction of the total power in the illumination is in a spectral range of from about 580 to about 780 nm.

11. A method of operating an automated optical inspection system to separate soft-centered potato chips from a mixture including soft-centered potato chips and fully cooked potato chips, comprising:

illuminating the mixture with illumination characterized by a spectral power distribution including a high intensity of power at wavelengths in the near infrared;

detecting reflections of wavelengths of the illumination in the near infrared from the mixture;

identifying a selected item in the mixture based on the detected reflections; and separating the selected item from the mixture with use of the identification.

12. The method of claim 11, further comprising producing the illumination with a hot-cathode rare gas discharge lamp.

13. The method of claim 12, wherein the fully cooked potato chips reflect more of the power of the illumination in the near infrared than do the soft-centered potato chips.

14. The method of claim 12, wherein substantially all of the power in the illumination is at wavelengths within a spectral range of from about 600 to about 800 nm.

15. The method of claim 12, wherein substantially all of the power in the illumination is at wavelengths within a spectral range of from about 650 to about 750 nm.

16. The method of claim 12, wherein a significant fraction of the total power in the illumination is in a spectral range of from about 650 to about 750 nm.

17. The method of claim 12, wherein the fully cooked potato chips reflect more of the power of the illumination at wavelengths within a spectral range of from about 600 to about 800 nm than do the soft-centered potato chips.

* * * * *